(12) United States Patent
Husain et al.

(10) Patent No.: US 8,425,854 B1
(45) Date of Patent: Apr. 23, 2013

(54) PROCESS FOR PROVIDING HYDROGEN TO A SYNTHESIS GAS CONVERSION REACTION

(75) Inventors: Shabbir Husain, Emeryville, CA (US); Charles Kibby, Benicia, CA (US); Lixin You, Sugar Land, TX (US); Babak Fayyaz-Najafi, Danville, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 53 days.

(21) Appl. No.: 13/224,600

(22) Filed: Oct. 7, 2011

(51) Int. Cl.
*B01J 7/00* (2006.01)
*B01J 8/00* (2006.01)

(52) U.S. Cl.
USPC ............ 422/239; 422/637; 422/626; 422/658

(58) Field of Classification Search .................. 422/239, 422/626, 637, 658
See application file for complete search history.

(56) References Cited

U.S. PATENT DOCUMENTS

| 4,181,675 | A | 1/1980 | Makin et al. |
| 2004/0181313 | A1 | 9/2004 | Mohedas et al. |
| 2011/0160315 | A1 | 6/2011 | Kibby et al. |

OTHER PUBLICATIONS

PCT/US2012/030932, International Search Report, mailing date Sep. 25, 2012, pp. 1-8.

*Primary Examiner* — Jafar Parsa
(74) *Attorney, Agent, or Firm* — Karen DiDomenicis; Richard Schulte (57) ABSTRACT

A synthesis gas conversion process for carrying out the process is disclosed. A hydrogen-containing sweep gas is caused to flow across a water permselective membrane adjacent a synthesis gas conversion reaction zone in which synthesis gas is contacted with a catalyst and converted to effluent including water. Water is removed from the reaction zone through the membrane. The sweep gas has sufficient hydrogen partial pressure to cause hydrogen to pass through the membrane into the reaction zone.

2 Claims, 7 Drawing Sheets

PROCESS FOR PROVIDING HYDROGEN TO A SYNTHESIS GAS CONVERSION REACTION

FIELD

The present invention relates to methods wherein water and hydrocarbon products are produced as part of a synthesis gas conversion and the water is removed in situ from the reaction products using a membrane.

BACKGROUND

Removal of water is a key issue to be addressed in synthesis gas conversion reactions. For instance, water is a primary by-product in a Fischer-Tropsch (FT) reaction and its presence is generally detrimental to the overall efficiency of the FT reaction. In an FT reaction, a synthesis gas mixture of carbon monoxide (CO) and hydrogen gas ($H_2$), referred to hereinafter as "syngas," is converted in the presence of an FT catalyst (most commonly iron- or cobalt-based) into hydrocarbon products, water and other byproducts. The syngas may be generated from a number of carbon containing sources such as natural gas, coal or bio-mass. It is often desirable to convert these carbon sources into a liquid hydrocarbon mixture from their original gas or solid states.

As the FT reaction occurs at relatively high temperature, the water produced is generally in the form of water vapor. Produced water vapor reduces the partial pressures of FT reactants, thus affecting reaction kinetics and reducing reaction rates. Water vapor is also detrimental to the life of FT catalysts, and especially in high partial pressures, leads to the oxidation of the catalyst and the sintering of the catalyst support, resulting in a reduction in the catalyst activity. Due to these adverse effects of water on the FT reaction, conventional FT fixed bed reactors have a relatively low rate of per pass CO conversion to limit high water partial pressures in the reactor. Conventional FT fixed bed reactors separate water from other reaction products and unreacted CO and $H_2$ gas after they exit the reactor's outlet. The unreacted CO is often recycled back to an FT reactor inlet so that it may again potentially be converted into a hydrocarbon, at the cost of increased throughputs, resulting in larger reactors.

Efforts with respect to in situ dehydration in conversion of syngas to hydrocarbon products and water have been described. U.S. patent application Ser. No. 12/342,799 (Fayyaz-Najafi et al.), assigned to Chevron U.S.A. Inc., hereby incorporated by reference in its entirety, describes improved designs for FT reactors, in which water is removed in situ using a membrane and wherein heat management issues are also addressed.

Another issue to be addressed in synthesis gas conversion reactions is control of the ratio of hydrogen to carbon monoxide ($H_2/CO$) in the syngas, as this affects the product distribution. When this ratio is too high, reaction products include undesirably high levels of methane and light gas. When this ratio is too low, reaction products include undesirably high levels of olefin and oxygenates. Additionally, consumption of hydrogen in the FT reactor occurs rapidly in the initial or upstream section of the reactor thereby lowering the partial pressure of hydrogen and thus the reaction rate and the $H_2/CO$ ratio in the downstream section of the reactor. Although the downstream end of the reactor has available heat removal capacity, this capacity remains unused when this section of the reactor is hydrogen starved.

It would be desirable to provide an improved process for the in situ removal of water from a synthesis gas conversion reactor such as an FT reactor. It would be further desirable to simultaneously provide for the addition of hydrogen at a controlled rate along the length of such a reactor to maintain sufficiently high hydrogen to carbon monoxide ratio to overcome the aforementioned current design constraints, thereby increasing the productivity of the reactor.

SUMMARY

In one aspect, the present invention relates to a synthesis gas conversion process in which a feed of synthesis gas comprising hydrogen and carbon monoxide is contacted with a synthesis gas conversion catalyst in a reaction zone in which the hydrogen and carbon monoxide react to form reaction products including water. The water is removed from the reaction products through a membrane in communication with the reaction zone, said membrane having a retentate side facing the reaction zone and a permeate side opposite the retentate side. A sweep gas containing hydrogen is caused to flow across the permeate side of the membrane at a hydrogen partial pressure sufficient to cause hydrogen to pass from the permeate side to the reaction zone.

In another aspect, the present invention relates to a system including a reactor having a housing and a membrane within the housing which defines a reaction zone and a sweep zone, the reaction zone adapted to convert syngas into products including hydrocarbons and water vapor in the presence of an appropriate catalyst, the membrane allowing the water vapor to permeate from the reaction zone to the sweep zone and a sweep gas to permeate from the sweep zone to the reaction zone. The system further includes a control system including a controller, at least one pressure sensor in communication with the controller for sensing the pressure in at least one of the reaction zone and the sweep zone, and a valve in communication with the controller for controlling sweep gas introduced into the sweep zone.

BRIEF DESCRIPTION OF THE DRAWINGS

These and other objects, features and advantages of the present invention will become better understood with regard to the following description, appended claims and accompanying drawings where:

DETAILED DESCRIPTION

In one embodiment, the disclosed process provides a synthesis gas conversion process including the in situ removal of water from a reactor using a water permselective membrane. By "wa-ter permselective membrane" is meant a membrane which allows water to pass there through prefe-rentially relative to other components. A syngas feed is supplied to a reaction zone within a reactor in which hydrogen and carbon monoxide, in the presence of a synthesis gas conversion catalyst, react to form an effluent including light gas, liquid hydrocarbon products and water. The present process can be adapted to various syngas compositions, including syngas with a relatively low $H_2$/CO ratio, which allows the use of the same design in different operations. The syngas may, for example, be obtained from natural gas, and also from peat, coal, biomass, or other hydrocarbon fractions by processes like gasification, autothermal reforming, catalytic or non-catalytic partial oxidation. The synthesis gas conversion reaction can be, by way of example and not limitation, any reaction in which water is produced, including, for example, a Fischer-Tropsch reaction, a methanol synthesis reaction or a dimethyl ether (DME) synthesis reaction.

The reaction zone can be within a fixed bed synthesis gas conversion reactor tube loaded with synthesis gas conversion catalyst. The effluent is then separated. The light gas, or tail gas, can optionally be recycled to the reaction zone. The hydrocarbons are removed from the reactor as product. The majority of water vapor is removed from the reactor in situ through a water permselective membrane in communication with the reaction zone. The membrane has a retentate side facing the reaction zone and a permeate side opposite the retentate side, i.e., facing away from the reaction zone. The membrane allows water vapor to readily pass there through from the reaction zone while inhibiting the passage of other reactants and products.

In operation, a syngas feed is introduced at the upstream end of the reactor into the reaction zone. Under suitable reaction conditions, desired synthesis gas conversion reactions, e.g., Fischer Tropsch reactions, occur. Reaction products can include hydrocarbon products of varying carbon chain lengths, $CO_2$ and water and a variety of other compounds. Under these conditions, the water is in the form of water vapor. Accordingly, water vapor preferentially passes through the water permselective membrane as a permeate stream while the other reaction products and unreacted feed preferentially remain in the reaction zone and are eventually discharged as a part of a retentate stream through the downstream end of the reactor. Ideally, unreacted $H_2$ and CO will be separated from the discharged retentate stream and recycled to the upstream portion of reaction zone and/or to a syngas reformer using processes known in the art.

Suitable water permselective membranes can be selected from zeolite membranes, ceramic membranes, polymeric membranes and composite membranes. Composite membranes include composites of ceramic and polymeric materials, composites of metallic and polymeric materials, and composites of ionic liquids and porous supports. In another embodiment zeolite membranes can be used, for instance Linde type 4A zeolite membranes such as those available from Mitsui Engineering & Shipbuilding Co., Ltd, Japan, and Fraunhofer Institute for Ceramic Technologies and Systems IKTS, Germany. Suitable membranes have a water/carbon monoxide selectivity of at least 10, even at least 100. Suitable membranes have a water permeance of at least 1000 GPU (gas permeation units), even at least 4000 GPU. One GPU is defined as the gas or vapor flow rate through a material per unit area and per unit of pressure difference across the material, with the unit defined as $10^{-6}$ $cm^3(stp).cm^{-2}.s^{-1}.cmHg^{-1}$. The membrane can be supported by a porous support, such as a ceramic, polymeric or metal support. The water permeance can be constant across the length of the membrane, or in some embodiments, the water permeance can be caused to vary across at least one dimension of the membrane in order to increase the water removal in the downstream sections of the reactor, since most of the water accumulation occurs in the downstream portion of the reactor. For example, the membrane may be coaxial about a longitudinally extending axis and the permeance of the membrane may increase in a downstream axial direction. In one embodiment, this can be accomplished by employing multiple membrane segments along the length of the reactor, each segment having a different water permeance. Alternatively, the membrane can be in the general shape of a cone having a smaller diameter at its upstream end portion and a larger diameter at its downstream end portion such that the membrane surface area varies along the length of the reactor. The concept of a conical membrane in a membrane reactor is disclosed in co-pending U.S. patent application Ser. No. 12/342,799 (Fayyaz-Najafi et al.), hereby incorporated by reference in its entirety. In such an embodiment, a membrane assembly having a porous generally conical shaped support member supporting a membrane will replace the membrane tube of FIG. 1. The radius of this membrane assembly increases from its upstream end to it downstream end. By way of example and not limitation, the membrane may be other shapes where the area perpendicular to the axis increases in the downstream direction, such as a parabolic cone as opposed to a purely frustoconical shape.

A sweep gas containing hydrogen is caused to flow across the permeate side of the mem-brane at a pressure sufficient to cause hydrogen to pass from the permeate side of the membrane to the reaction zone along the length of the reactor, either continuously or at discrete locations. The sweep gas contains a high partial pressure of hydrogen gas and permeation of hydrogen to the reac-tion zone occurs when the hydrogen partial pressure on the permeate side is higher than the hydro-gen partial pressure on the retentate side facing the reaction zone. Not only is hydrogen inhibited from "leaking" out of the reaction zone through the water removal membrane, thus having a nega-tive impact on productivity, but hydrogen is actually added to the reaction zone, thus enhancing conversion of the synthesis gas.

The flow rate of the sweep gas (volumetric or molar) can be between about 10 and about 200%, even between about 40 and about 100%, of the flow rate of the syngas feed, i.e., the ratio of the sweep gas flow rate to the feed flow rate can be between about 0.10 and about 2.0, even between 0.40 and 1.0. The flow rate of the sweep gas is thus calculated based on the flow rate of the feed. When the flow rate of the sweep gas is too low, water cannot be removed effectively since the driving force causing water to cross the membrane would be insufficient to remove water effective-ly. The sweep gas and the syngas feed can flow in either co-current or counter-current directions relative to one another. That is, the sweep gas may flow downstream in the reactor while the hy-drogen passes upstream from the downstream portion of the reactor. Alternatively, both the syngas feed and the hydrogen gas can be introduced relative to the upstream portion of the reactor.

Figure 1:
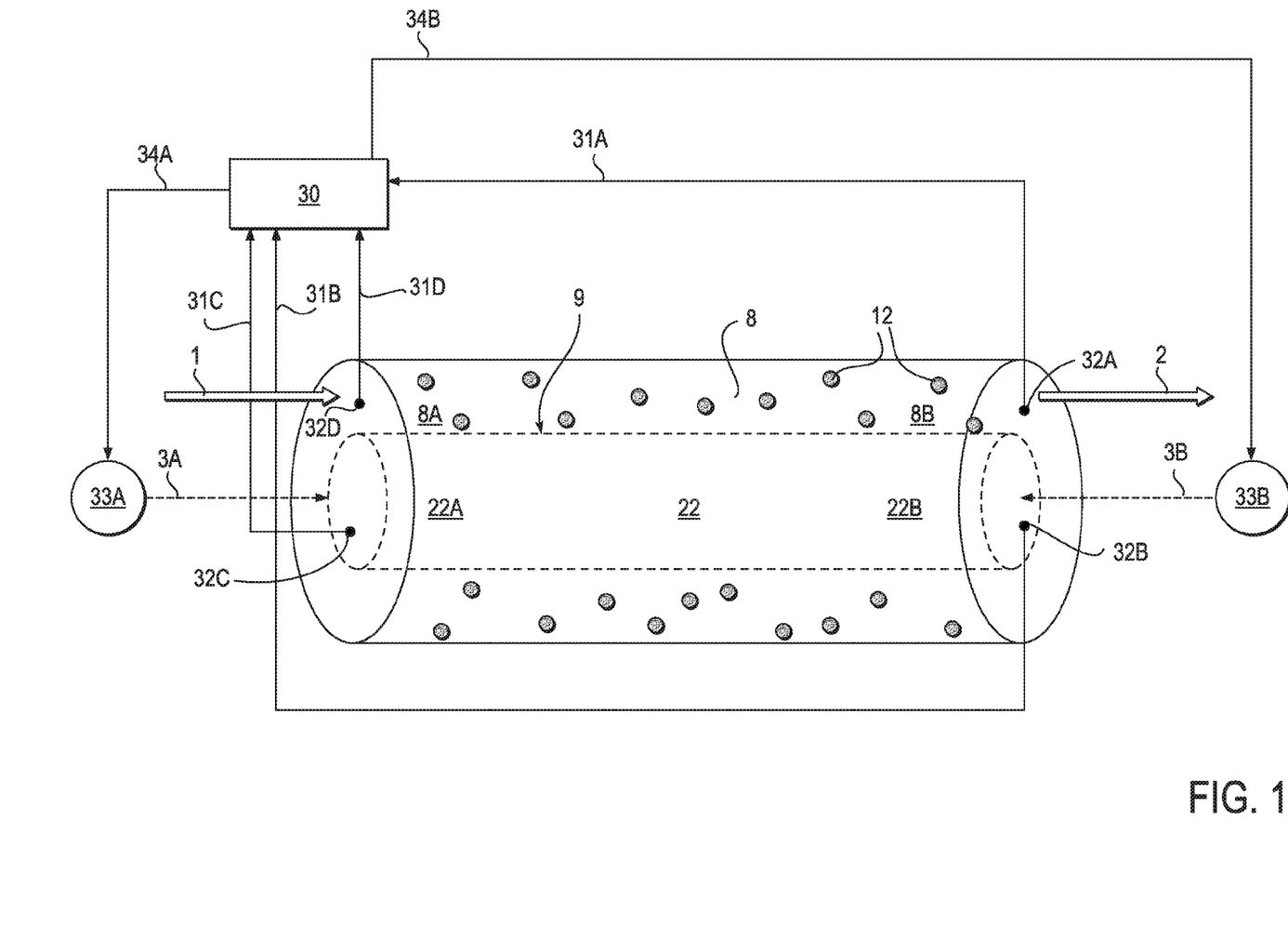
FIG. 1 is an illustration of a membrane tube employed in a membrane reactor according to one embodiment of the invention.

The addition of hydrogen to the reaction zone is controlled by the difference in hydrogen partial pressures between the reaction zone and the sweep zone. To control the hydrogen/carbon monoxide molar ratio within a desired range, hydrogen addition to the reaction zone can be mini-mized near the reactor inlet and maximized near the reactor outlet. A simple representation of a tu-bular membrane element in FIG. 1 is used to illustrate the relevant pressure conditions. The location generally near the reactor inlet in the reaction zone 8 is described as the upstream reaction zone 8A, while the location generally near the reactor outlet in the reaction zone is described as the down-stream reaction zone 8B. The location generally near the reactor inlet in the sweep zone 22 is described as the upstream sweep zone 22A, while the location generally near the reactor outlet in the sweep zone is described as downstream sweep zone 22B. Syngas feed (also referred to as feed) 1 is fed to the reaction zone. Sweep gas can be fed to flow along membrane 9 either co-currently (i.e., in the same direction as feed 1) as indicated by 3A or counter-currently (i.e., in the opposite direction as feed 1) as indicated by 3B.

When the sweep gas is fed in a co-current configuration (as indicated by 3A), the partial pressure of hydrogen in the upstream reaction zone 8A is desirably roughly equivalent to the partial pressure of hydrogen in the upstream sweep zone 22A, in order to minimize loss or addition of hy-drogen to the reaction zone in the region near the reactor inlet. In order to maximize the addition of hydrogen to the reaction zone in the region near the reactor outlet, the partial pressure of hydrogen in the downstream sweep zone 22B is desirably greater than the partial pressure of hydrogen in the downstream reaction zone 8B. As a result of the reaction and consumption of hydrogen in the reac-tion zone, the partial pressure of hydrogen in the downstream reaction zone 8B is less than the par-tial pressure of hydrogen in the upstream reaction zone 8A. Similarly, the partial pressure of hydro-gen in the sweep zone is lower in the downstream sweep zone 22B than in the upstream sweep zone 22A.

When the sweep gas is fed in a counter-current configuration (as indicated by 3B), the above relative pressure conditions also apply, with the exception that the partial pressure of hydrogen in the sweep zone is higher in the downstream sweep zone 22B than in the upstream sweep zone 22A. In either co-current or counter-current sweep gas flow, the pressure of the sweep gas at the reactor inlet is controlled to minimize loss or addition of hydrogen to the upstream reaction zone 8A, while the pressure of the sweep gas near the reactor outlet is controlled to maximize the addition of hydrogen to the downstream reaction zone 8B.

In one embodiment, gas samples from reactor outlet 32A, downstream sweep zone location (inlet or outlet, depending on whether sweep gas flow is counter-current or co-current, respectively) 32B, upstream sweep zone location (outlet or inlet) 32C and reactor inlet 32D can be analyzed by an analyzer (not shown), for example a gas chromatogram (GC), to determine the concentration of hydrogen at the inlet and outlet of both the reaction zone and the sweep zone. The total gas pres-sure can also be measured by pressure sensors at one or more of these four locations, 32A-D. Information on the total pressure measurements and the hydrogen concentration measurements can be sent to a controller 30 using lines 31A-D. Using this information, the controller 30 can determine the partial pressure of hydrogen at each of the four locations. The controller can then send signals to pressure control valves via lines 34A and/or 34B, for example, to control a pressure control valve 33A and/or 33B in communication with a sweep gas inlet (not shown) to control the pressure and consequently the hydrogen partial pressure within the sweep zone 22 as desired. The pressure con-trol valve(s) in the downstream portion of the sweep zone can be sized to allow a sweep gas flow between about 10% and 200% of the feed gas flow to the reaction zone. Additional valves can be brought online as needed to accommodate higher flows, can provide greater flexibility in allowing both pressure and flow to be controlled in the sweep zone.

Figure 2:
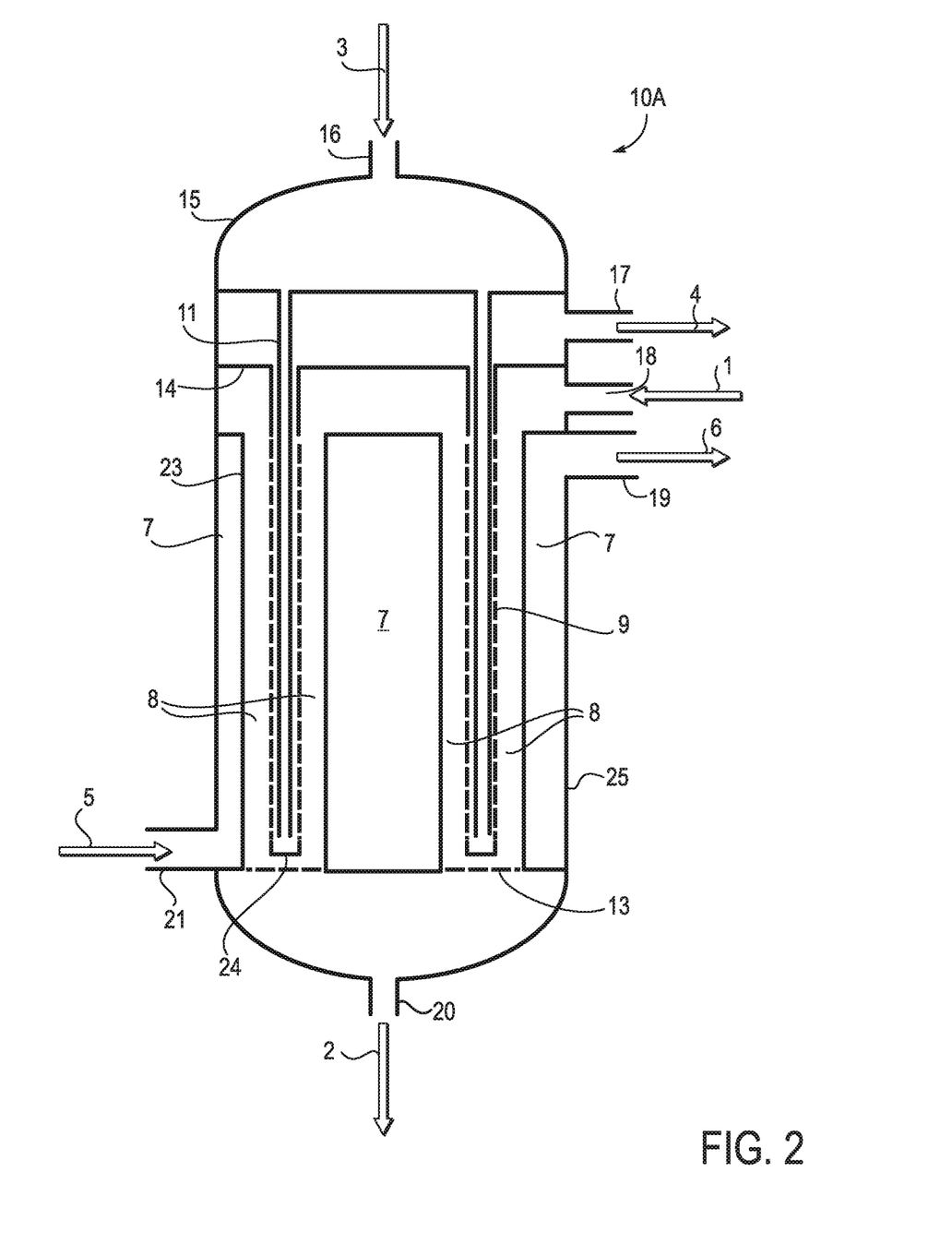
FIG. 2 is a schematic drawing of a multi-tubular fixed bed synthesis gas conversion reactor according to one embodiment of the invention, including an in situ water removal membrane with a hydrogen-containing sweep gas.

In one embodiment, as shown in FIG. 2 and described in detail hereinafter, the reaction zone is located within a fixed bed reactor tube in which the synthesis gas conversion catalyst occupies an annular volume within the tube which is bounded on the outside by the wall of the reactor tube and on the inside by a membrane tube formed by the membrane. This is also referred to as a double tube-in-tube reactor design (tube in a tube in a tube). The membrane tube has an outer retentate side and an inner permeate side. In this embodiment, sweep gas is supplied through a pipe or conduit extending into the membrane tube such that the sweep gas is caused to flow inside the membrane tube, between the conduit and the membrane tube. In one embodiment, the disclosed process further provides for the addition of hydrogen to the reactor. In this embodiment, the sweep gas has a hydrogen partial pressure sufficiently high to cause hydrogen to pass from the permeate side through the membrane to the desired location in the reaction zone. The double tube-in-tube reactor design as described above and shown in FIG. 2 can be used. While the figure illustrates two tubes, it will be understood by those skilled in the art that the reactor may include many such tubes. By adding hydrogen to the reaction zone along the length of the reactor, a more constant $H_2/CO$ ratio can be maintained along the length of the reactor. The rate of hydrogen addition can be controlled by adjusting the hydrogen partial pressure driving force across a given membrane.

One embodiment of an FT reactor having a water removal membrane and utilizing a hydrogen-containing sweep gas is shown in FIG. 2. In operation, a syngas feed 1 is introduced into reactor 10A by way of reactant inlet 18 and into reaction zone 8. Reactants ($H_2$ and CO) come in from the top of the tubular reactor and flow downward into the catalyst bed. FT conversions take place in reaction zone 8 with FT products being produced including hydrocarbon and water vapor. The reaction zone 8 is contained at the lower end by perforated plate 13. The fluid FT products stream 2 is then allowed to exit FT reactor 10A by way of products outlet 20. These products can be then separated with unreacted CO and $H_2$ gas being recycled (not shown) back to reactant inlet 18.

In this embodiment, the FT reactor 10A has the capability of providing a sweep gas to enhance the in situ water vapor removal from FT reactor 10A. Reactor 10A has catalyst (not shown) packed into a reaction zone 8 formed between tubes 23 and 9. Partially mounted in the FT reactor is a membrane assembly 14 which has multiple tubes with porous walls 9 and an end plate 24 which seals the tubes, thereby defining a water vapor zone. Membrane materials, such as a zeolite membrane, are affixed to a support wall to permit water vapor to readily pass from reaction zone 8, through water permselective material or membrane 9 and into the water vapor zone. The top of membrane assembly 14 is a tube sheet (i.e., a circular plate with multiple holes drilled with specific pattern to accommodate the membrane tubes). By way of example and not limitation, the outer diameter of tube 23 can be, for example, in the range of 1.05-2.375 inches (2.7-6.0 cm), and even 1.315-1.9 inches (3.3-4.8 cm). The outer diameter of tube 9 can be in the range of 0.675-1.9 inches (1.7-4.8 cm), and even 0.84-1.66 inches (2.1-4.2 cm).

An outer shell 25 provides a water bath chamber 7, surrounding reaction zone 8. Water 5 is introduced into cooling water inlet 21 and surrounds reaction zone 8 to maintain the temperature in reactor 10 at a predetermined temperature. Heat supplied from reaction zone 8 transforms the water into steam 6 which exits the reactor by way of steam outlet 19. Water inlet 21 and steam outlet 19 are in fluid communication with water chamber 7. Controlling the water flow and the pressure and boiling temperature of water in water bath chamber 7 allows the temperature in reaction zone 8 to be controlled.

A sweep gas assembly 11 is provided for introducing a hydrogen-containing sweep gas 3 into the water vapor zone within each membrane tube 9. Sweep gas assembly 11 has multiple conduits which are inserted into the water vapor zone within each membrane tube 9 and serve to deliver sweep gas 3 to the lower end of the water vapor zone. Sweep gas assembly 11 is in fluid communication with an end cap 15 which has a sweep gas inlet 16.

A significant portion of the water vapor produced passes through membrane 9 into the water vapor zone on the inner permeate side of each membrane. The partial pressure of water in the water vapor zone is maintained at a relatively low value compared to reaction zone 8, in part due to the sweep gas. Sweep gas is introduced into sweep gas inlet 16; passes inside the sweep gas conduits of sweep gas assembly 11 to the lower end of each water vapor zone; and then flows counter current to the syngas feed along membrane 9 to assist in the removal of water vapor. The sweep gas 3 contains reactant hydrogen gas. The combined water vapor and sweep gas steam 4 is then swept out of the reactor by way of water vapor outlet 17.

Figure 3:
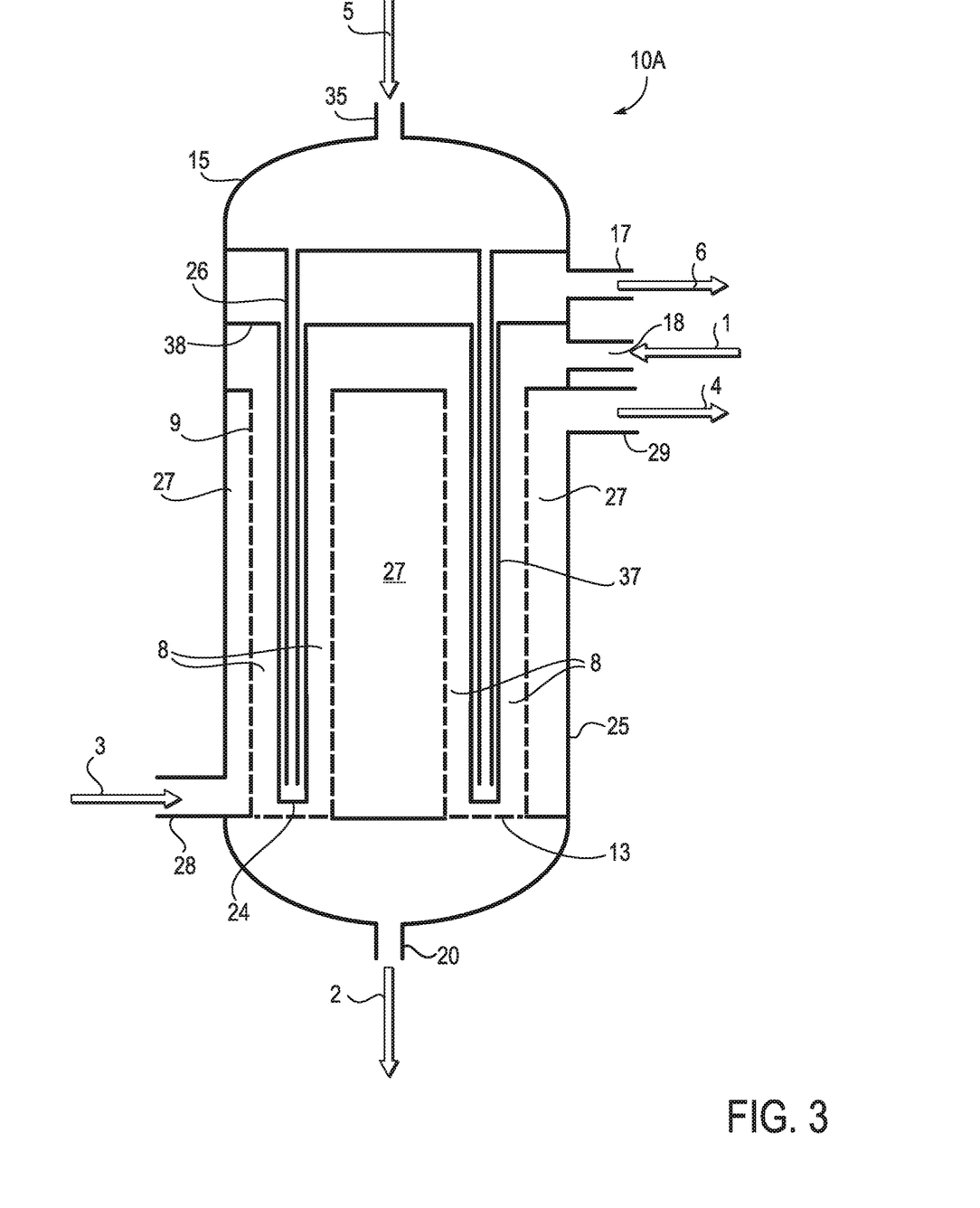
FIG. 3 is a schematic drawing of a multi-tubular fixed bed synthesis gas conversion reactor, according to another embodiment of the invention, including an in situ water removal membrane in fluid communication with a hydrogen-containing sweep gas.

In an alternative embodiment, as shown in FIG. 3, reactor 10B operates in a similar manner as reactor 10A described above and illustrated in FIG. 2, except that in this embodiment, the location of the cooling water and the sweep gas relative to the reaction zone are reversed, such that the cooling water cools from an internal space within each reaction zone 8 and the sweep gas passes across the membrane tube 9 which is disposed about each reaction zone 8. Sweep gas 3 enters through sweep gas inlet 28 and flows through sweep gas zone 27, across the outer surface of membrane tube 9, and exits as gas stream 4 through sweep gas outlet 29.

A cooling water assembly is provided for introducing cooling water 5 into the internal space within each reaction zone 8. Cooling water assembly conduits 26 are inserted into the internal space within each reaction zone 8 and serve to deliver cooling water 5 to the lower end of the reaction zone. The internal space within each reaction zone 8 is defined by conduit 37 of tube sheet assembly 38. Cooling water assembly 26 is in fluid communication with an end cap 15 which has a cooling water inlet 35. Cooling water stream 6 exits through cooling water outlet 36.

Figure 4:
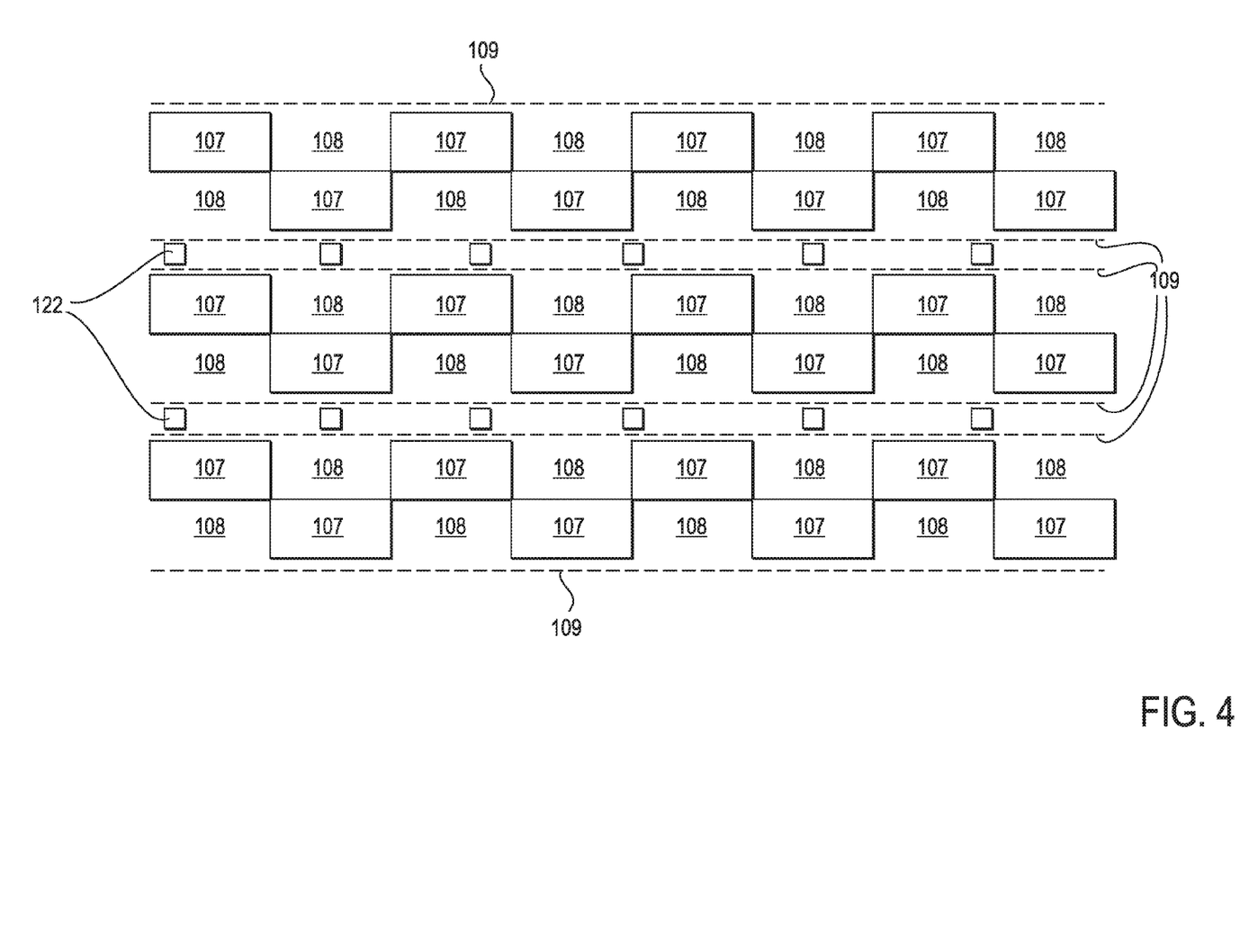
FIG. 4 is a schematic drawing of a plate type synthesis gas conversion reactor according to yet another embodiment of the invention, including an in situ water removal membrane in fluid communication with a hydrogen-containing sweep gas.

In yet another alternative embodiment, as shown in FIG. 4, the reaction zone 108 is in the form of a channel located within a plate type reactor 110 having multiple alternating layers of reaction zone channels 108, cooling channels 107 and water permselective membranes 109. Each layer is kept separated by porous spacers 122. Syngas feed is introduced to the reaction zone channels 108 which contain catalyst. Reaction products including water are produced in reaction zone channels 108, and water is removed across membranes 109. In this embodiment, hydrogen sweep gas is introduced across the face of membranes 109. Water or another suitable coolant occupies cooling channels 107, thus controlling the temperature of reaction zone channels 108. FIGS. 2, 3 and 4 illustrate only three of many possible configurations, as would be apparent to one skilled in the art.

By controlling the rate of hydrogen addition, it has been found that the present process provides for a number of advantages as compared with a similar process with no hydrogen sweep gas used. In some embodiments, the rate of carbon monoxide conversion is increased as a result of added hydrogen in the reaction zone and a higher ratio of hydrogen to carbon monoxide in the unconverted syngas along the length of the reactor. In some embodiments, the present process allows for a reduced reactor length, a reduced volume of catalyst and/or a reduced number of reactor tubes since the conversion rate is enhanced. In some embodiments, the present process allows for a reduced amount of tail gas recycle since the conversion is enhanced, thus desirably reducing the need for compression of tail gas to be returned to the reactor.

In a Fischer-Tropsch process, typically, the reaction conditions include using a suitable FT catalyst such as an iron-based or cobalt-based catalyst or a mixture of both. In one embodiment, the reaction occurs at a temperature between about 160° C. and about 350° C., even between about 200° C. and about 250° C. In another embodiment, the temperature is kept at about 180-220° C. when cobalt-based catalysts are used and about 250-280° C. when iron-based catalysts are used. The pressure in the reaction zone is between about 1 and about 100 atmospheres, even between about 10 atmospheres and about 30 atmospheres. The pressure on the permeate side of the water removal membrane is maintained at a lower pressure than that in the reaction zone where the FT conversions take place. A hydrogen-containing sweep gas is used to further reduce the partial pressure of water on the permeate side of the water removal membrane and hence increase the driving force for the water separation. The gaseous hourly space velocity of the reaction is less than about 20,000 volumes of syngas per volume of catalyst per hour. The syngas feed has a $H_2/CO$ ratio between about 0.5 and about 2.5, even between amount 1.0 and about 2.0. In general, the upper limit of the $H_2/CO$ ratio will be the usage ratio of the unit. The usage ratio is the ratio in which hydrogen and CO are used in a reactor which varies depending on the nature of the catalyst and the process conditions applied.

EXAMPLES

Figure 5:
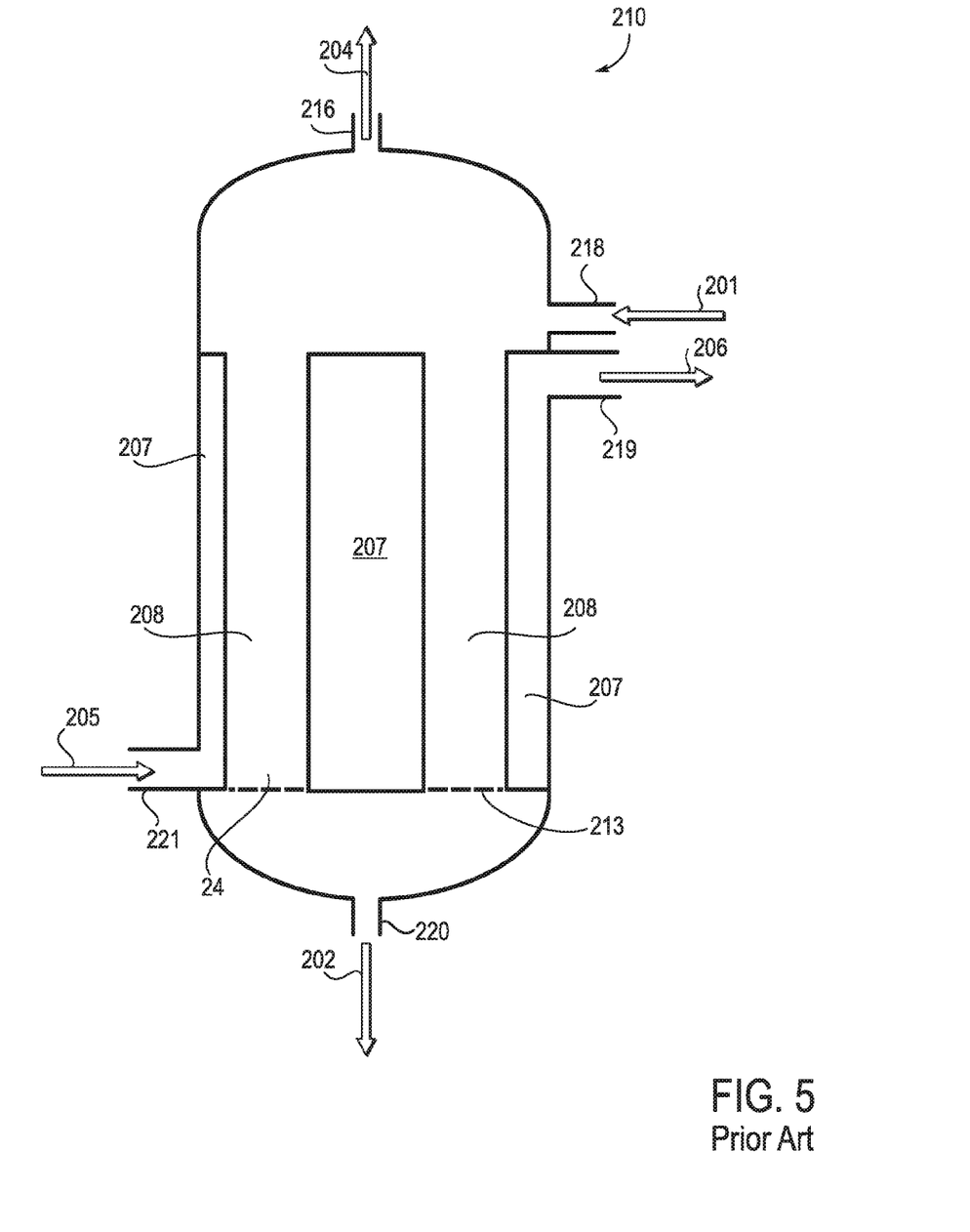
FIG. 5 is a schematic drawing of a conventional multi-tubular fixed bed synthesis gas conversion reactor, not including an in situ water removal membrane.

Computer modeling was used to compare an embodiment using a pure hydrogen sweep gas with a comparable membrane reactor using a nitrogen sweep gas and with a comparable non-membrane FT reactor. A double tube-in-tube type reactor as illustrated in FIG. 2 was used for the embodiments using sweep gas. A comparable non-membrane reactor is defined as a reactor having an equivalent size and configuration as the reactor shown in FIG. 2, and generally having the configuration of reactor 210 as shown in FIG. 5. There is no membrane tube and no provisions for a sweep gas. In operation, a syngas feed 201 is introduced into reactor 210 by way of reactant inlet 218 and into reaction zone 208 containing catalyst (not shown). Reactants enter the top of the tubular reactor and flow downward into the catalyst bed. FT conversions take place in reaction zone 208 with FT products being produced and water vapor. The reaction zone 208 is contained at the lower end by perforated plate 213. The products stream 202 is then allowed to exit the reactor by way of products outlet 220. Water bath chamber 207 surrounds reaction zone 208. Water 205 is introduced into cooling water inlet 221 and surrounds reaction zone 208 to maintain the temperature in the reactor at a predetermined temperature. Heat supplied from the reaction zone transforms the water into steam 206 which exits the reactor by way of steam outlet 219. Water inlet 221 and steam outlet 219 are in fluid communication with water chamber 207. Controlling the water flow and the pressure and boiling temperature of water in water bath chamber 207 allows the temperature in reaction zone 208 to be controlled.

A simulation was conducted using software based on Aspen Custom Modeler, commercially available from Aspen Technology Inc., Burlington, Mass. The membrane transport properties, operating conditions and reactor dimensions assumed are listed in Table 1. Reaction kinetics for a cobalt-based FT catalyst containing 7.5 wt % Co and 0.19 wt % Ru on a support containing 80 wt % ZSM-12 zeolite and 20 wt % $Al_2O_3$ was assumed. The simulation was conducted for a single tube-in-tube reactor, with the results multiplied by 100,000, assuming a reactor with 100,000 reaction tubes. The syngas ($H_2/CO=1.6$) flow rate per tube was assumed to be 0.99108 lb-mol/hr.

Sweep gas ratio is defined as the mole of sweep gas per total mole of feed gas.

TABLE 1

| Membrane properties | |
| --- | --- |
| $H_2O$ permeance | $1.38 \times 10^{-5}$ mol/cm$^2$-bar-sec (4400 GPU) |
| $H_2O/H_2$ selectivity | 50 |
| $H_2O/CO$ selectivity | 125 |
| $H_2O/CO_2$ selectivity | 60 |
| $H_2O/N_2$ selectivity | 150 |
| $H_2O/CH_4$ selectivity | 200 |
| Operating conditions | |
| $H_2/CO$ ratio of the feed | 1.6 |
| Pressure | 20 bar (2000 kPa) |
| Temperature | 208° C. |
| Sweep gas ratio | 67% |
| Sweep gas pressure | 8 bar (800 kPa) |
| Tube-in-tube reactor design | |
| Reactor tube outer diameter | 1.66 in (4.2 cm) |
| Reactor tube inner diameter | 1.426 in (3.6 cm) |
| Membrane tube outer diameter | 1.05 in (2.7 cm) |
| Membrane tube inner diameter | 0.83 in (2.1 cm) |
| Reactor length | 36 ft (11 m) |

Figure 6:
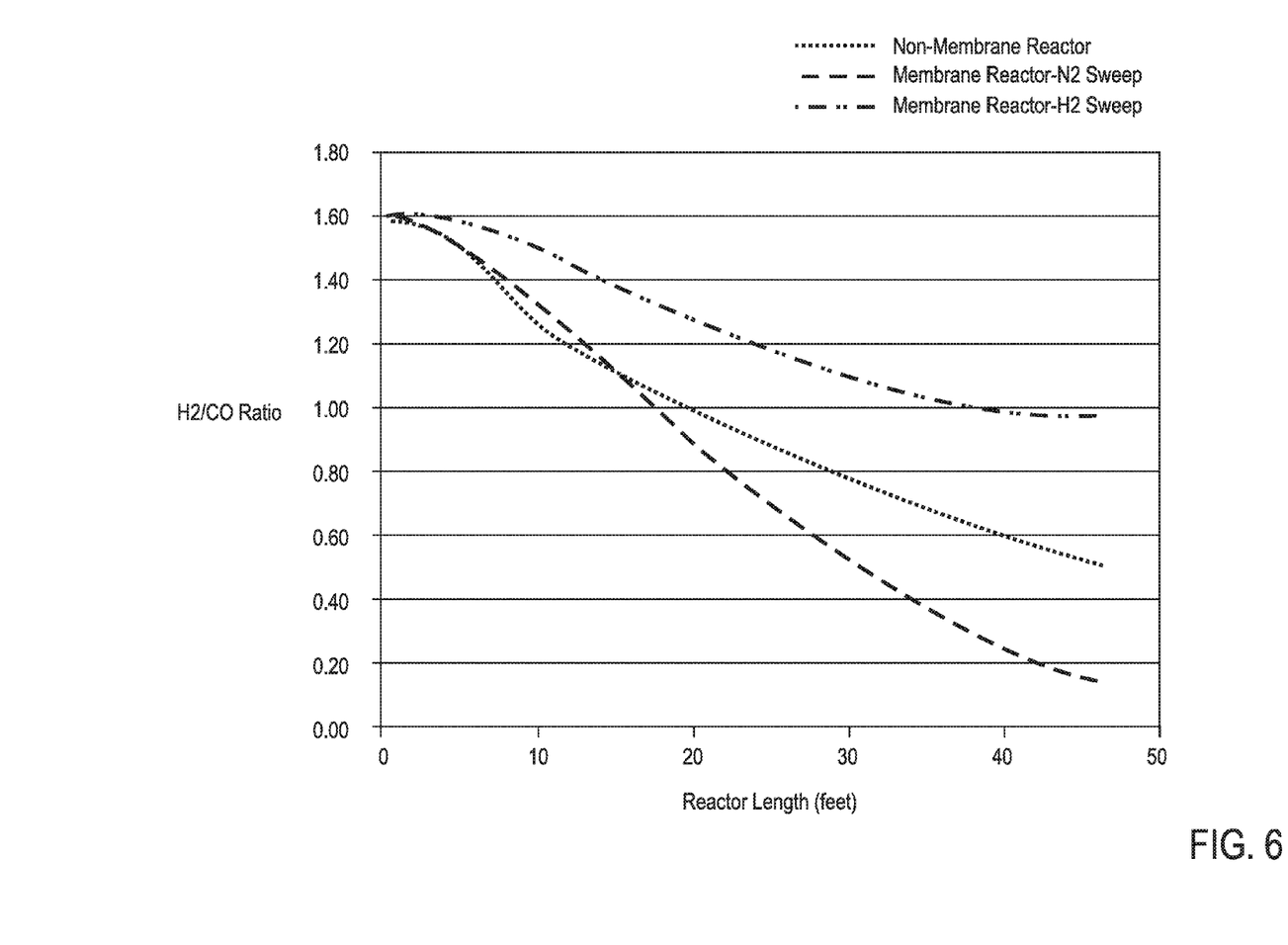
FIG. 6 is a graph comparing the $H_2/CO$ ratios along the length of a Fischer-Tropsch fixed bed reactor for three scenarios: utilizing a water removal membrane with a hydrogen-containing sweep gas, utilizing a water removal membrane with a nitrogen-containing sweep gas and not utilizing a water removal membrane.

FIG. 6 is a graph comparing the $H_2/CO$ ratios along the length of a Fischer-Tropsch fixed bed reactor for three scenarios: utilizing a water removal membrane with a hydrogen-containing sweep gas, utilizing a water removal membrane with a nitrogen-containing sweep gas and not utilizing a water removal membrane, with a $H_2/CO$ ratio of the feed of 1.6. The results indicate that a higher $H_2/CO$ ratio is maintained in the hydrogen sweep membrane reactor along the reactor length versus both the nitrogen sweep membrane reactor and the non-membrane reactor. The higher $H_2/CO$ ratio near the downstream end of the reactor is believed to reduce the formation of olefins and oxygenates in the reactor. Reduced formation of olefins may result in lower upgrade costs since downstream hydrotreatment can be avoided or reduced. Reduced formation of oxygenates may result in lower water treatment costs.

Figure 7:
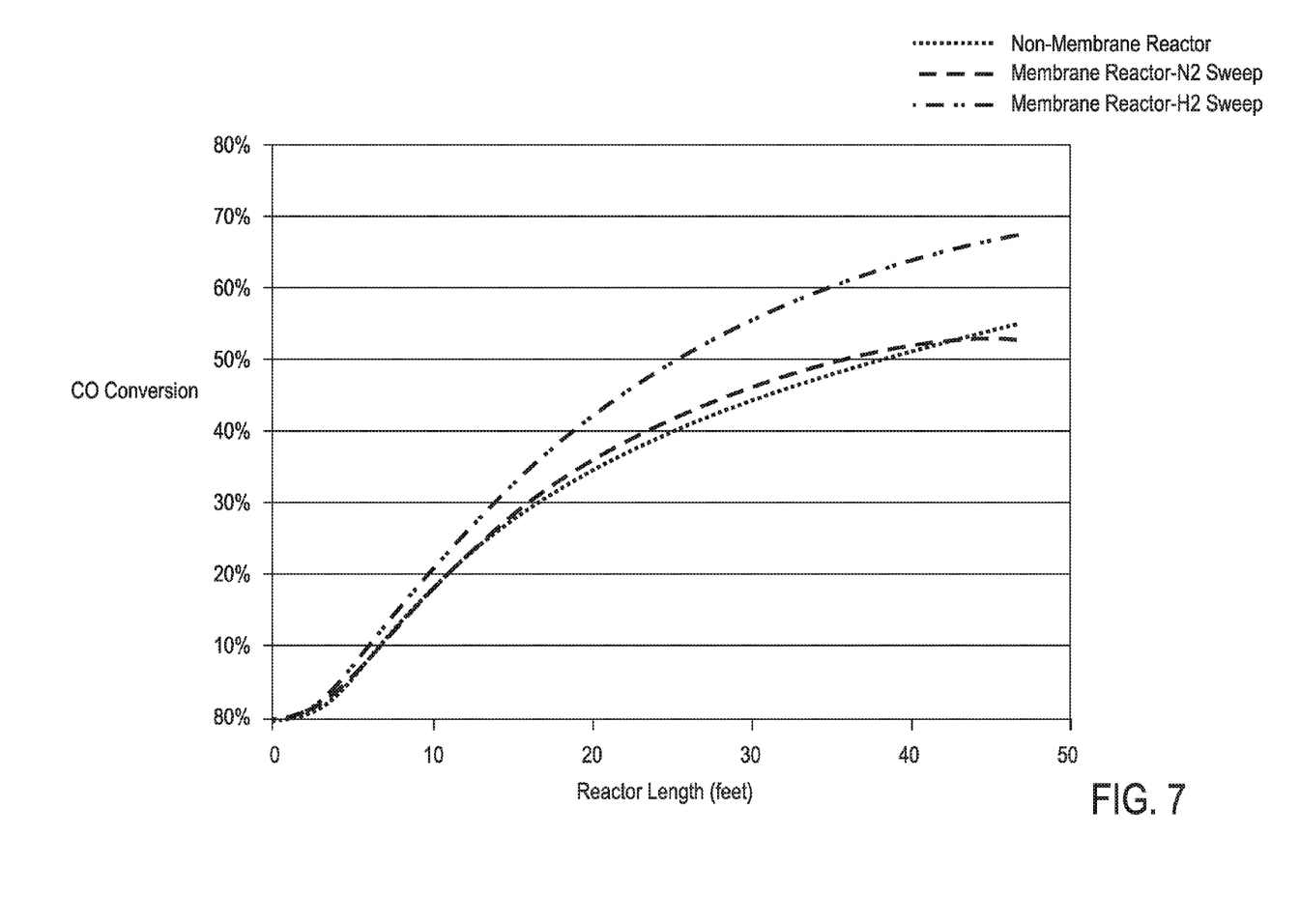
FIG. 7 is a graph comparing the CO conversion rates along the length of a Fischer-Tropsch fixed bed reactor for three scenarios: utilizing a water removal membrane with a hydrogen-containing sweep gas, utilizing a water removal membrane with a nitrogen-containing sweep gas and not utilizing a water removal membrane.

FIG. 7 is a graph comparing the CO conversion rates along the length of a Fischer-Tropsch fixed bed reactor for the same three scenarios. The results indicate that hydrogen permeating from the reaction zone into the membrane in the nitrogen sweep case reduces the single pass CO conversion of the reactor for a given reactor length. Considerably higher CO conversion is achieved for a hydrogen sweep membrane reactor as compared with both the nitrogen sweep membrane reactor and the non-membrane reactor.

Higher levels of CO conversion result in reduced need for recycle, increased hydrocarbon product yields, higher carbon efficiency and lower reactor feed rate. Table 2 lists the benefits of the use of a water removal membrane with hydrogen-containing sweep gas (also referred to as "hydrogen sweep membrane reactor") when compared with a reactor not utilizing a membrane and sweep gas (also referred to as "non-membrane reactor"). "Product" refers to the amount of produced liquid hydrocarbons. "Recycle ratio" refers to the ratio of recycle stream flow rate to the fresh syngas flow rate. The recycle stream is the stream of unreacted CO, $H_2$, inert gases ($N_2$, $CO_2$) and light hydrocarbons from the reactor outlet after condensing liquid products and water, the recycle stream being recycled to the reactor inlet. "Carbon efficiency" refers to the amount of carbon in the final product divided by the carbon in the feed.

TABLE 2

| | Hydrogen sweep membrane reactor | Non-membrane reactor | % delta, hydrogen sweep membrane reactor vs. non-membrane reactor |
| --- | --- | --- | --- |
| Reactor length, feet (meters) | 36 (11 m) | 39 (12 m) | −7.7 |
| Number of reactor tubes | 100,000 | 120,000 | −16.7 |
| Overall CO conversion, mol % | 90.9 | 85.8 | +6.3 |
| CO single pass conversion, mol % | 60 | 51 | +17.6 |
| Product, barrels per day | 37,883 | 35,351 | +7.2 |
| Recycle ratio | 0.766 | 0.900 | −14.9 |
| Carbon efficiency, % | 77.0 | 71.2 | +8.1 |
| Reactor feed flow rate, lb-mol/hr | 99,108 | 123,597 | −19.8 |
| Water partial pressure at reactor end, bar | 1.3 (130 kPa) | 5.6 (560 kPa) | −76.8 |

While in the foregoing specification this invention has been described in relation to certain preferred embodiments thereof, and many details have been set forth for purpose of illustration, it will be apparent to those skilled in the art that the invention is susceptible to alteration and that certain other details described herein can vary considerably without departing from the basic principles of the invention.

What is claimed is:

1. A system comprising:
   a) a reactor including a housing and a membrane within the housing which defines a reaction zone and a sweep zone, the reaction zone adapted to convert syngas into products including hydrocarbons and water vapor in the presence of an appropriate catalyst, the membrane allowing the water vapor to permeate from the reaction zone to the sweep zone and a sweep gas to permeate from the sweep zone to the reaction zone; and
   b) a control system including a controller, at least one pressure sensor in communication with the controller for sensing the pressure in at least one of the reaction zone and the sweep zone, and a valve in communication with the controller for controlling sweep gas introduced into the sweep zone.

2. The system of claim 1, further comprising a gas chromatogam in communication with the controller and in communication with at least one location within the reactor for determining hydrogen concentration at the at least one location.

* * * * *